(12) United States Patent
Keel et al.

(10) Patent No.: US 8,968,208 B2
(45) Date of Patent: Mar. 3, 2015

(54) GUIDED MYOCARDIAL SUBSTRATE CHARACTERIZATION AND INFARCT SCAR LOCATION

(71) Applicant: Pacesetter, Inc., Sylmar, CA (US)

(72) Inventors: Allen Keel, San Francisco, CA (US); Rupinder Bharmi, Canyon Country, CA (US); Stuart Rosenberg, Castaic, CA (US); Hedi Razavi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 94 days.

(21) Appl. No.: 13/681,802

(22) Filed: Nov. 20, 2012

(65) Prior Publication Data

US 2014/0142406 A1    May 22, 2014

(51) Int. Cl.
| | |
|---|---|
| *A61B 5/0402* | (2006.01) |
| *A61B 5/02* | (2006.01) |
| *A61B 5/04* | (2006.01) |
| *A61B 5/06* | (2006.01) |
| *A61B 5/107* | (2006.01) |
| *A61B 5/11* | (2006.01) |
| *A61B 5/00* | (2006.01) |
| *A61B 5/0456* | (2006.01) |

(52) U.S. Cl.
CPC ......... *A61B 5/02028* (2013.01); *A61B 5/04007* (2013.01); *A61B 5/0402* (2013.01); *A61B 5/06* (2013.01); *A61B 5/1072* (2013.01); *A61B 5/1102* (2013.01); *A61B 5/6851* (2013.01); *A61B 5/6852* (2013.01); *A61B 5/7225* (2013.01); *A61B 5/6869* (2013.01); *A61B 5/6885* (2013.01); *A61B 5/0053* (2013.01); *A61B 5/0456* (2013.01); *A61B 5/062* (2013.01); *A61B 5/107* (2013.01); *A61B 5/1107* (2013.01); *A61B 5/1114* (2013.01)

USPC .......... 600/508; 600/509; 600/512; 600/513; 600/527

(58) Field of Classification Search
CPC ............ A61B 2017/00243; A61B 2017/1076; A61B 2017/6869; A61B 17/00234; A61B 5/02; A61B 5/0245; A61B 5/0084; A61B 2018/00351; A61B 2018/00357; A61B 5/00; A61B 5/05; A61B 5/061; A61B 5/076; A61B 5/103; A61B 5/107; A61B 5/1072; A61N 1/3627; A61N 1/0587; A61N 1/05; A61N 1/0597; A61N 1/36514; A61N 1/3702; A61N 1/36578; A61N 1/37; A61F 2/2481; A61F 2/02; A61F 2/2487; A61M 2230/04; A61M 2210/125
USPC ......................... 600/508–509, 512–513, 527
See application file for complete search history.

(56) References Cited

U.S. PATENT DOCUMENTS

| | | | |
|---|---|---|---|
| 6,701,176 B1 | 3/2004 | Halperin et al. | |
| 6,957,101 B2 | 10/2005 | Porath et al. | |
| 7,003,348 B1 * | 2/2006 | Brewer et al. ................... | 607/17 |
| 7,155,271 B2 | 12/2006 | Halperin et al. | |

(Continued)

FOREIGN PATENT DOCUMENTS

| | | |
|---|---|---|
| EP | 1421913 A1 | 5/2004 |
| EP | 1504713 A1 | 9/2005 |

*Primary Examiner* — Deborah Malamud

(57) ABSTRACT

An apparatus and method for quantifying myocardial kinetics by positioning two sensors on a myocardial substrate site so that one sensor is directly opposing the other along a ventricular wall; tracking a relative displacement between the two sensors; and determining whether there is an infarct based on the tracked relative displacement.

11 Claims, 8 Drawing Sheets

(56) References Cited

U.S. PATENT DOCUMENTS

| | | |
|---|---|---|
| 7,697,972 B2 | 4/2010 | Verard et al. |
| 8,046,052 B2 | 10/2011 | Verard et al. |
| 8,099,151 B2 | 1/2012 | Halperin et al. |
| 2003/0199755 A1 | 10/2003 | Halperin et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0097227 A1* | 4/2008 | Zdeblick et al. .............. 600/486 |
| 2009/0281439 A1 | 11/2009 | Harlev et al. |
| 2012/0065481 A1 | 3/2012 | Hunter et al. |

* cited by examiner

GUIDED MYOCARDIAL SUBSTRATE CHARACTERIZATION AND INFARCT SCAR LOCATION

FIELD

This disclosure relates generally to techniques for assessing the health of cardiac tissues. More particularly, the disclosure relates to guided myocardial substrate characterization and infarct scar location.

BACKGROUND

Myocardial tissue viability is currently characterized by either analysis of electrograms (EGMs) or by non-invasive imaging modalities such as echocardiography and delayed enhancement MRI (DE-MRI). However, these imaging methods may have limitations. For example, echocardiography is an indirect measure of infarcted tissue and suffers from intra-observer and inter-observer variability. DE-MRI carries high costs, and device compatibility remains an issue not completely resolved. Also, EGMs provide inferential information based on a fractionated signal and is limited by the number of sites covered. Left ventricular lead implantation requires the lead to be placed accurately in a coronary vein that leads to optimal benefit and does not compromise the safety of the patient. For example, a left ventricular lead implant near or at an infarct zone may lead to non-efficacious pacing due to the electrical inactively of the non-viable tissue. In one example, the goal may be to pace at or near the site of a scar tissue.

Ablation for scar-related/ischemic ventricular tachycardia is a technique that requires precision in the location of the lesion creation. It is typically guided by electro-anatomical mapping. However, the mechanical component of information from the chamber is not taken into account. Thus, there is a need to improve the accuracy of substrate characterization and localization and provide guidance on decision making in regard to ablation or cardiac resynchronization therapy (CRT) lead implant location, for example, with respect to infarct scar zones.

SUMMARY

According to one aspect, a method for quantifying myocardial kinetics including: positioning a first sensor and a second sensor on a myocardial substrate site so that the first sensor is directly opposing the second sensor along a ventricular wall; tracking a relative displacement between the first sensor and the second sensor; and determining whether the myocardial substrate site includes an infarct based on the tracked relative displacement.

According to another aspect, a system for quantifying myocardial kinetics including: one or more processors; memory; and control logic, implemented at least in part by the one or more processors and the memory, configured to: position a first sensor and a second sensor on a myocardial substrate site so that the first sensor is directly opposing the second sensor along a ventricular wall; track a relative displacement between the first sensor and the second sensor; and determine whether the myocardial substrate site includes an infarct based on the tracked relative displacement.

According to another aspect, a method for determining tissue health through application of forces including: applying a plurality of successive forces through a tool to the myocardial tissue in a region of interest (ROI), and holding each of the plurality of successive force for a duration of time, wherein the tool includes a tip and a sensor positioned on the tip; measuring a plurality of deflections of the tip of the tool, wherein each of the plurality of deflections corresponds to each of the plurality of successive forces applied to the myocardial tissue in the ROI; and determining the health condition of the myocardial tissue based on the plurality of deflections.

According to another aspect, a system for determining tissue health through application of forces including: one or more processors; memory; and control logic, implemented at least in part by the one or more processors and the memory, configured to: apply a plurality of successive forces through a tool to the myocardial tissue in a region of interest (ROI), and hold each of the plurality of successive force for a duration of time, wherein the tool includes a tip and a sensor positioned on the tip; measure a plurality of deflections of the tip of the tool, wherein each of the plurality of deflections corresponds to each of the plurality of successive forces applied to the myocardial tissue in the ROI; and determine the health condition of the myocardial tissue based on the plurality of deflections.

According to another aspect, a method for measuring temporal difference including: measuring position information and orientation information using a sensor for a duration of time; determining a peak position information and a peak orientation information from the measured position information and the measured orientation information; calculating a temporal difference between the peak position information and the peak orientation information; and comparing the temporal difference to a threshold.

According to another aspect, a system for measuring temporal difference including: one or more processors; memory; and logic, implemented at least in part by the one or more processors and the memory, configured to: measure position information and orientation information using a sensor for a duration of time; determine a peak position information and a peak orientation information from the measured position information and the measured orientation information; calculate a temporal difference between the peak position information and the peak orientation information; and compare the temporal difference to a threshold.

Advantages of the present disclosure may include eliminating the dependency on costly and time-consuming preoperative imaging and assisting medical personnel to make ablation and/or implant decisions during a cardiac procedure. Another advantage may include improved accuracy of substrate characterization and localization. In one example, multiple signals may be used to quantify regional myocardial kinetics and characterize myocardial substrate. In one example, endocardial and epicardial sensors may be used to quantify wall thickening and transmurality of infarct scar. In one example, sensors on a tool (e.g., an ablation catheter) tip may be used to localize infarct scar based on responses to different forces exerted on the cardiac tissue. In one example, phase difference from position and orientation of a sensor may be used to differentiate an infarct scar from healthy tissue.

It is understood that other aspects will become readily apparent to those skilled in the art from the following detailed description, wherein it is shown and described various aspects by way of illustration. The drawings and detailed description are to be regarded as illustrative in nature and not as restrictive.

DETAILED DESCRIPTION

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for the purpose of providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the present disclosure.

Accurate characterization of a myocardial substrate is an important feature in a medical personnel's decision to implant lead targets at the myocardial site. For example, determining that a myocardial substrate is unhealthy for lead target implantation can minimize or eliminate non-efficacious pacing due to the electrical inactivity of the non-viable tissue. Additionally, the ability to locate accurately an infarct scar for ablation during a cardiac procedure can improve the overall success of the surgical outcome. Techniques for guided myocardial substrate characterization and infarct scar localization may also minimize the dependency on costly and time-consuming pre-operative imaging.

Figure 1:
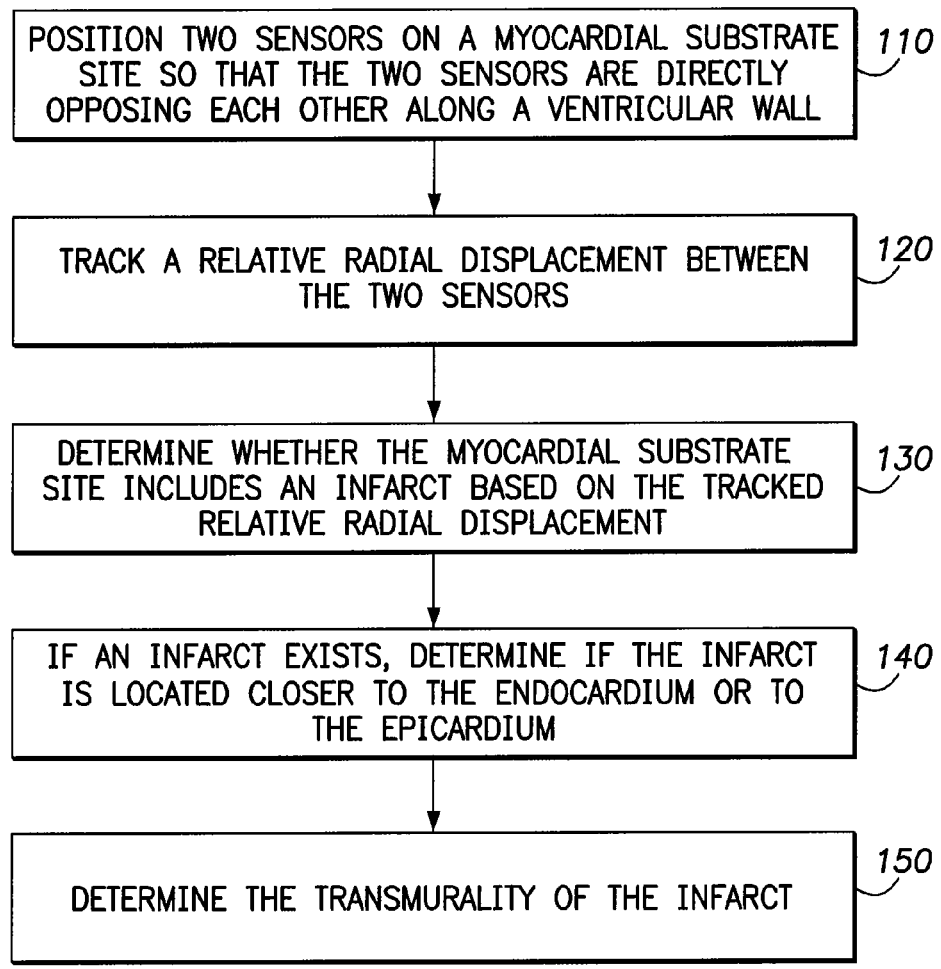
FIG. 1 illustrates an example flow diagram for quantifying myocardial kinetics.

In one aspect, two signals may be used to quantify myocardial kinetics. The myocardial kinetic information may be used to characterize the myocardial substrate, for example, for ablation or for cardiac resynchronization therapy (CRT) lead implantation. FIG. 1 illustrates an example flow diagram for quantifying myocardial kinetics. In block 110, position two sensors on a myocardial substrate site so that the two sensors are directly opposing each other along a ventricular wall. In one example, fluoroscopy is used to detect visually the placements of the sensors. In another example, placements of the sensors are navigated with the aid of pre-determined imaging of the myocardial substrate site. In yet another example, fluoroscopy and pre-determined imaging may be used together for the placements of the sensors. Other aids for the placements of the sensors may be used without deviating from the scope and spirit of the present disclosure.

The sensors may be positioned on the myocardial substrate site via a tool (such as, but not limited to, a guide wire or a stylet and/or a catheter, for example, an electrophysiology catheter). In one example, one sensor is epicardially-placed (e.g., via transvenous or direct epicardial implantation route) and the other sensor is endocardially-placed. For example, one sensor is advanced to a location in the coronary sinus (CS), e.g., lateral/postero-lateral location while the other sensor is advanced to the endocardial surface across from the sensor located in the CS. One skilled in the art would understand that there are many entry points on the patient's body for placement of the epicardially-placed sensor and the endocardial-placed sensor which are practiced by medical personnel.

In block 120, track a relative displacement (e.g., a radial displacement) between the two sensors. In one example, the sensors are electromagnetic sensors which measure electromagnetic field strengths for determining relative displacements. In another example, the sensors are ultrasonic sensors which measure acoustic waves for determining relative displacements. However, other sensor types may be used for the disclosed applications as understood by one skilled in the art. Also, although FIG. 1 is illustrated using two sensors, one skilled in the art would understand that additional sensors may be used without affecting the scope and spirit of the present disclosure.

In block 130, determine whether the myocardial substrate site includes an infarct based on the tracked relative displacement. In block 140, if an infarct exists, determine if the infarct is located closer to the endocardial or to the epicardial surface. In one example, this determination is based on the tracked relative displacement. For example, if the epicardially-placed sensor is being displaced significantly while the endocardially-placed sensor is akinetic, then the infarct can be deemed to be closer to the endocardial surface. For example, if the endocardially-placed sensor is being displaced significantly while the epicardially-placed sensor is akinetic, then the infarct can be deemed to be epicardially located. In one example, absolute sensor displacement for each of the sensors is measured relative to a predefined reference midline. In another example, absolute sensor displacement for each of the sensors is measured relative to an external reference, such as a third sensor or a transmitting source.

In block 150, determine the transmurality of the infarct. In one example, the electrocardiography (ECG) gated signals are used to compute wall thickness for determining transmurality. In another example, the electrocardiography (ECG) continuous motion signals are used to compute wall thickness for determining transmurality. In one example, the ECG signals are taken at end systole and at end diastole. In one aspect, determine the transmurality of the infarct based on the relative displacement between the first sensor and the second sensor at at least two time points synchronized with one or more cardiac electrical signals. Although the examples herein may refer to ECG signals, one skilled in the art would understand that intracardiac electrogram (IEGM) signals may be used in place of ECG signals. ECG and IEGM signals are examples of cardiac electrical signals.

In another example, measure a first systolic thickness ($L_{1s}$) (for example, using the first sensor) of a first layer relative to a reference midline at an end diastole and measure a second systolic thickness ($L_{2s}$) (for example, using the second sensor) of a second layer relative to the reference midline, and then compute a ratio $L_{1s}/L_{2s}$.

Figure 2:
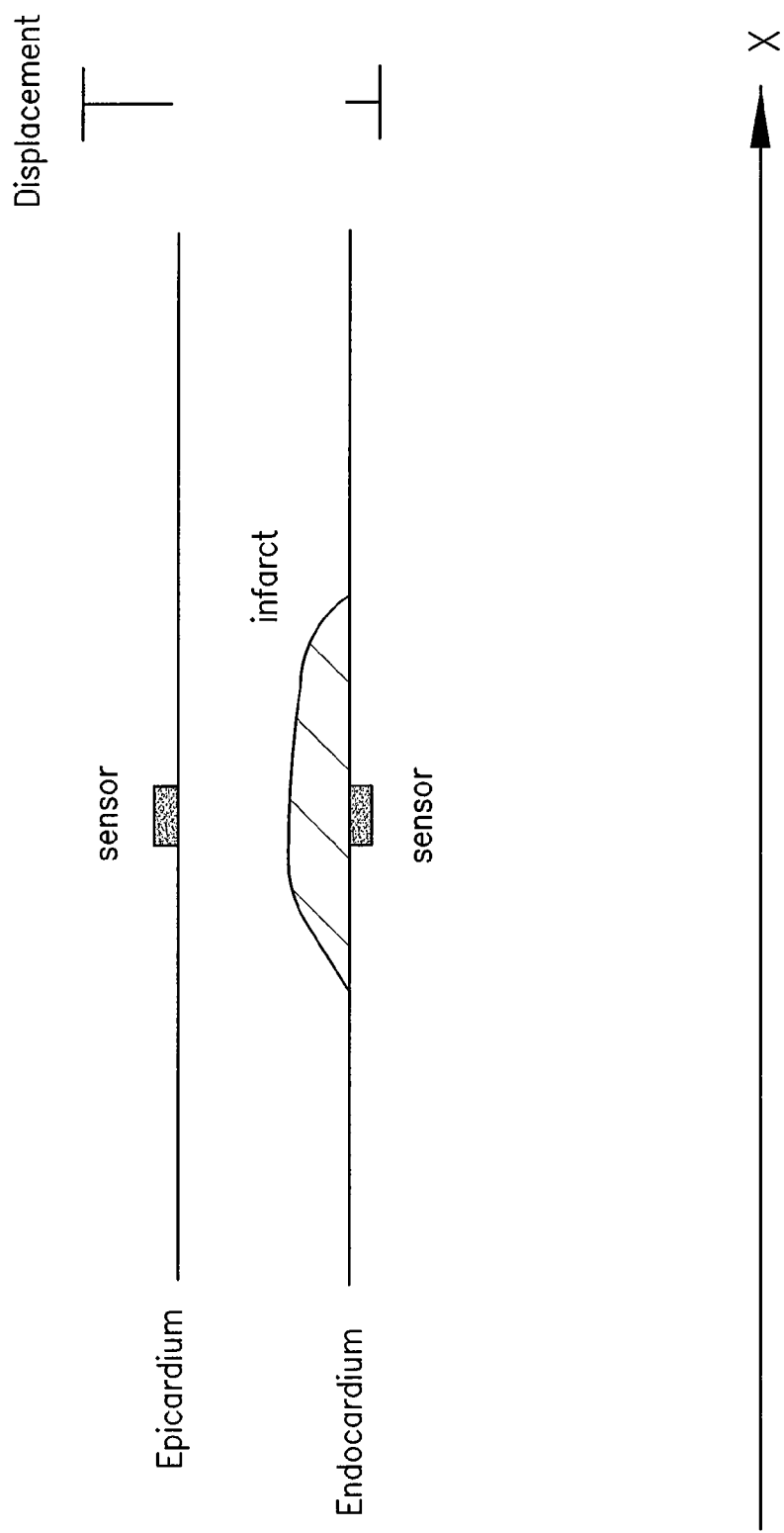
FIG. 2 illustrates an example showing the locations of two sensors relative to an infarct.

FIG. 2 illustrates an example showing the locations of two sensors relative to an infarct. As shown in FIG. 2, one sensor is positioned on the epicardium and the other sensor is positioned on the endocardium. The relative displacement between the two sensors is measured at discrete points along the heart wall, for example along the long axis or circumferentially about the heart. In FIG. 2, the X-axis represents position. The transmurality of the infarct scar may also be estimated. In one example, electrocardiography (ECG) gated signals from the two sensors are compared (thus yielding relative displacement) to provide the ventricular wall thickening information. A particular point of the cardiac cycle (e.g., end systole, end diastole, etc.) may be monitored. In another example, electrocardiography (ECG) continuous motion signals from the two sensors are compared (thus yielding relative displacement) to provide the ventricular wall thickening information.

Figure 3:
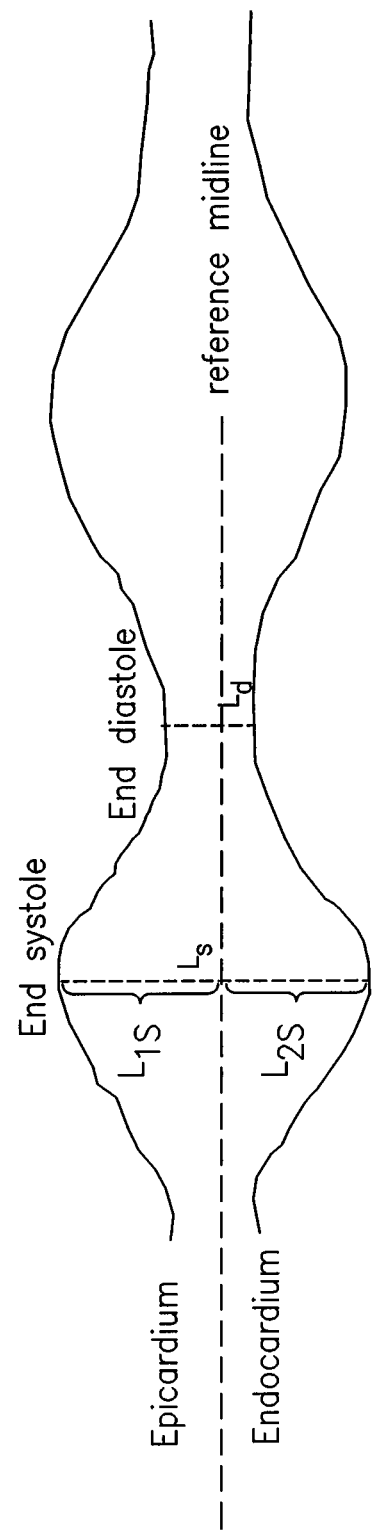
FIG. 3 illustrates an example of relative displacements as measured between an endocardially-placed sensor and an epicardially-placed sensor as measured at end systole and at end diastole.

FIG. 3 illustrates an example of relative displacements as measured between an endocardially-placed sensor and an epicardially-placed sensor as measured at end systole and at end diastole. With $L_s$ as the distance between the two sensors at end-systole and $L_d$ as the distance at end-diastole, the ventricular wall thickening (represented as a percentage) can be computed as $[(L_s-L_d)/L_s]*100$. For a healthy myocardium, the ventricular tissue will typically experience wall thickening at roughly 5-7% active strain in the radial (cross-sheet) direction. Percent wall thickening of less than roughly 5-7% may be identified as myocardium with scarring where the scar itself will have no active wall thickening. A measured active wall thickening of 5% to 0% is mapped respectively to 0% to 100% transmural scarring. Also, wall thickening of about 2.5% may correspond to approximately 50% transmural scarring. That is, approximately 0% wall thickening corresponds to approximately 100% transmural scar; 5% wall thickening corresponds to approximately 0% transmural scar; and 2.5% wall thickening corresponds to approximately 50% transmural scar.

Alternately, define $L_{1s}$ as the systolic thickness of one layer relative to a reference midline at end diastole, and $L_{2s}$ as the systolic thickness of the other layer relative to the same reference midline. The transmurality of the infarct scar may be computed as a ratio $L_{1s}/L_{2s}$. A transmurality of 1 indicates homogenous myocardial substrate health throughout the wall thickness, while a measure significantly less than 1 or more than 1 indicates differences in myocardial substrate health across the ventricular wall thickness.

In one aspect, an endocardial catheter equipped with a sensor is used during an ablation procedure. The endocardial catheter is navigated through the left ventricle chamber to a region of interest (ROI). Once the endocardial catheter is in proximity of the ROI, the testing of the site is conducted to determine the composition of cardiac tissue in the ROI. The tip of the endocardial catheter (which houses the sensor) contacts the myocardium tissue in the ROI at two or more varying amounts of forces, in succession. In one example, three varying amounts of forces are used in succession. Other quantities of varying amounts of forces may also be used. In one aspect, an epicardial catheter is used in place of the endocardial catheter of the above example. And, if the procedure is an implant procedure, a delivery tool (e.g., a guide wire or a stylet) may be used instead of an endocardial catheter or an epicardial catheter.

Figure 4:
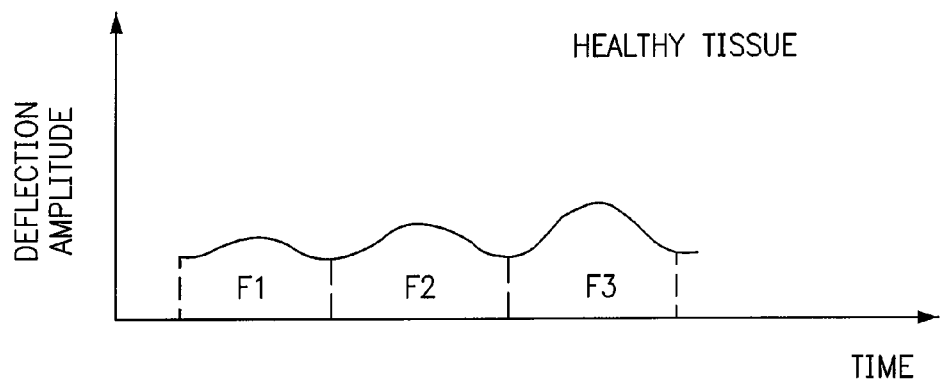
FIG. 4 illustrates an example of three varying forces applied in succession to healthy tissue and contrast to scarred tissue.
Figure 4:
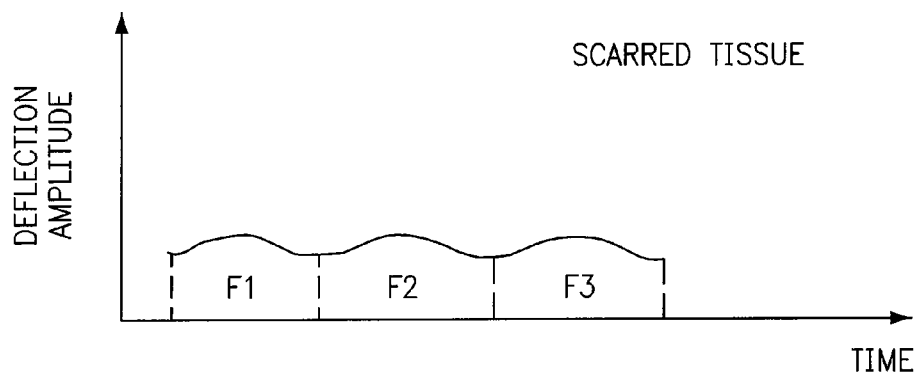

FIG. 4 illustrates an example of three varying forces applied in succession to healthy tissue and contrast to scarred tissue. In FIG. 4, the vertical axis is deflection amplitude and the horizontal axis is time. Shown in FIG. 4, $F_1$ is applied for an interval of time, followed by applying $F_2$ for the same amount of time and then followed by applying $F_3$, again for the same amount of time. In FIG. 4, $F_1$ is a force less than $F_2$ and less than $F_3$. And, $F_2$ is a force less than $F_3$. For each application of the force, the deflection on the tip is measured by the sensor as an indicator of deformation of the myocardium tissue. In one example, each application of the force is held for one cardiac cycle. The amount of force applied by the operator while holding the endocardial catheter in measuring the deflection on the tip should be approximately equal throughout the entire cardiac cycle for any given force application that the resultant deformation of the myocardium tissue in passive and active states may be assessed. Although one cardiac cycle is illustrated as an example, the present disclosure applies equally to less than one cardiac cycle, multiple cardiac cycles or fractions thereof. If the difference between deflection amplitude at peak diastole (or, for example, at peak systole) increases for corresponding increasing forces of successive force applications, then the myocardial tissue is labeled as healthy tissue (see FIG. 4). In this case, the healthy myocardial tissue is responsive (i.e., has different constitutive laws for passive and active states) while the scar tissue may be stiffer at baseline with no differentiation between passive and active (i.e. does not activate).

If the deflection amplitude remains constant for increasing forces of successive force applications, then the myocardial tissue is labeled as dead, i.e., scarred tissue (see FIG. 4). When the myocardial tissue is dead, the myocardial tissue is inactive and will not provide any reactive force to the perturbation of the force application. This is true, whether the force applications are made throughout diastole or systole since the myocardial tissue will have the same stiffness throughout a cardiac cycle. Borders or isthmuses between "healthy" and "scar" zones would indicate a potentially good burn sites for the ablation procedure.

In one example, multiple ROI may be tested for myocardial substrate characterization in order to determine the optimal location for ablation. Additionally, although the example of FIG. 4 shows three forces, other quantities of forces, for example, two forces or greater than three forces may be used at each ROI without deviating from the scope and spirit of the present disclosure.

Figure 5:
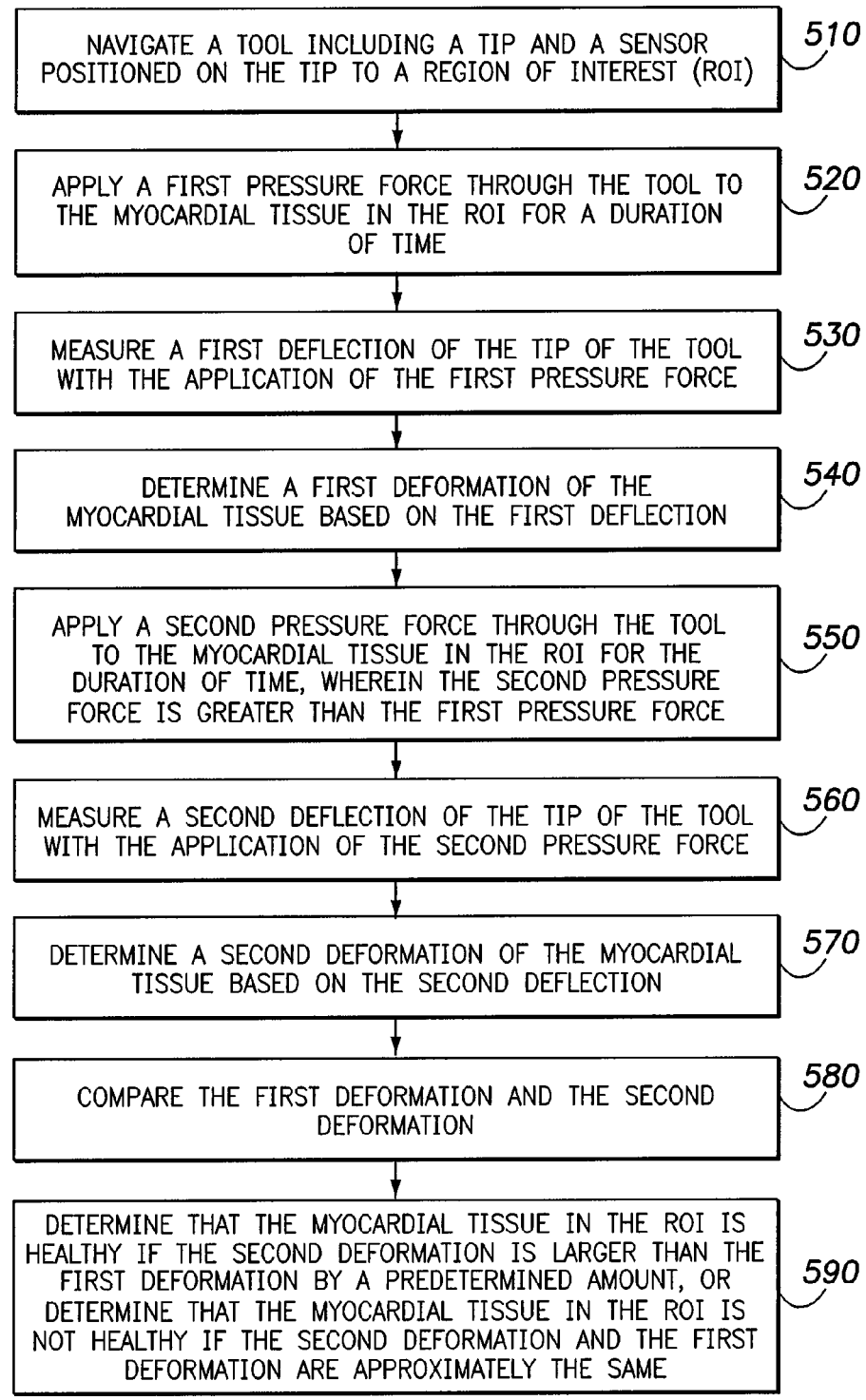
FIG. 5 illustrates an example flow diagram for determining tissue health through application of two varying amounts of forces in succession.

FIG. 5 illustrates an example flow diagram for determining tissue health through application of two varying amounts of forces in succession. In block 510, navigate a tool including a tip and a sensor positioned on the tip to a region of interest (ROI). In one example, the tool is an endocardial catheter or an epicardial catheter. In another example, the tool is a guide wire or a stylet. The sensor may be an electromagnetic sensor or an ultrasonic sensor. However, other tool types and/or sensor types may be used for the disclosed applications as understood by one skilled in the art.

In block 520, apply a first force through the tool to the myocardial tissue in the ROI for a duration of time. In one example, the duration of time is a cardiac cycle. In block 530, measure a first deflection of the tip of the tool with the application of the first force. In block 540, determine a first deformation of the myocardial tissue based on the first deflection. In block 550, apply a second force through the tool to the myocardial tissue in the ROI for the duration of time, wherein the second force is greater than the first force. In block 560, measure a second deflection of the tip of the tool with the application of the second force. In block 570, determine a second deformation of the myocardial tissue based on the second deflection. In block 580, compare the first deformation and the second deformation. In block 590, determine that the myocardial tissue in the ROI is healthy if the second deformation is larger than the first deformation by a predetermined amount, or determine that the myocardial tissue in the ROI is not healthy (e.g., scarred or an infarct) if the second deformation and the first deformation are approximately the same.

In one alternative case, the steps in blocks 540 and 570 are optional and not used. Instead, in this alternative case, in block 580, compare the first deflection and the second deflection. And, in this alternative case, in block 590, determine that the myocardial tissue in the ROI is healthy if the second deflection is larger than the first deflection by a predetermined amount, or determine that the myocardial tissue in the ROI is not healthy (e.g., scarred or an infarct) if the second deflection and the first deflection are approximately the same.

In one example, more than two forces are used; that is, the steps in blocks 520 through 540 are repeated multiple times with varying forces. With multiple forces applied to the myocardial tissue in the ROI, the myocardial tissue is determined to be healthy if the deformation increases with increased applied forces. And, the myocardial tissue is determined to be not healthy (e.g., scarred or an infarct) if the deformation remains approximately constant with increased applied forces. In one example, a set of multiple forces is applied to multiple regions of interest to determine an optimal location for ablation. In one example, the tool is either an endocardial catheter or an epicardial catheter (e.g., for use in ablation) or a transvenous guide wire or stylet (e.g., for use for lead implantation).

Figure 6:
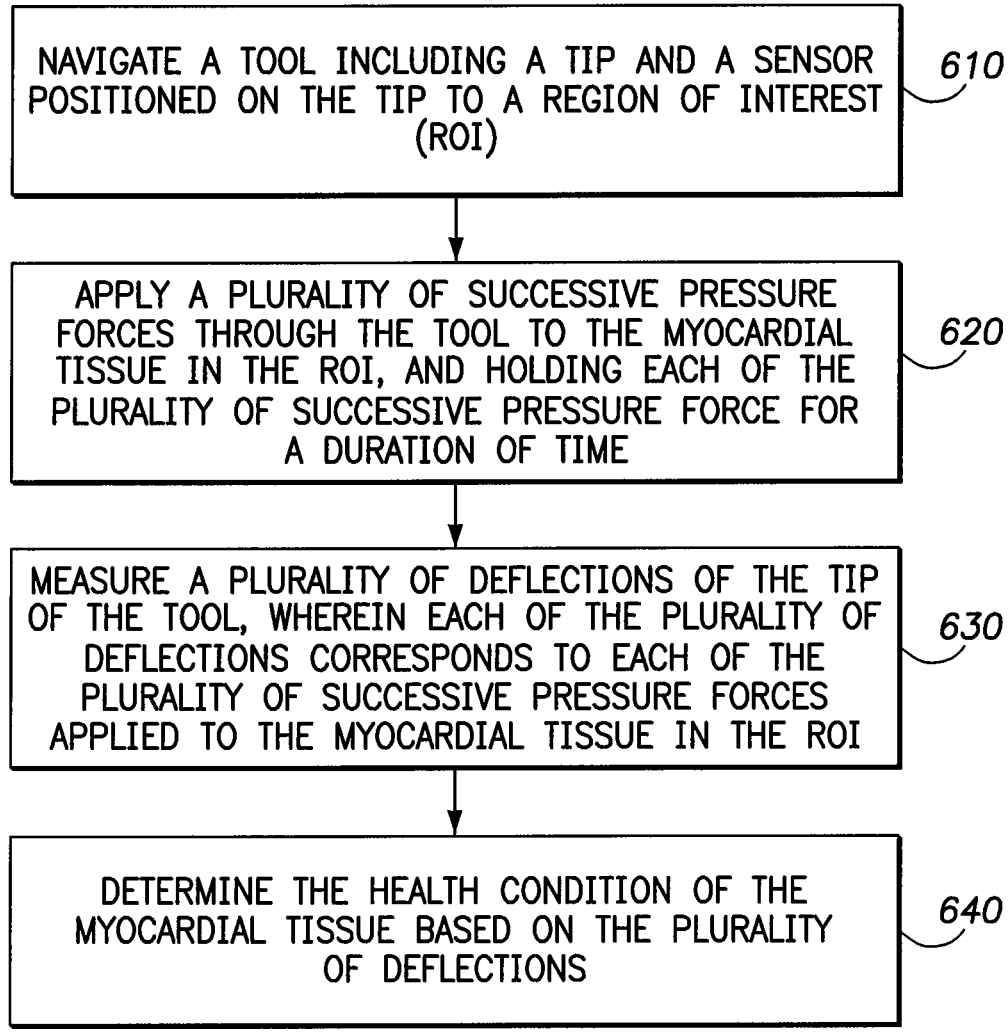
FIG. 6 illustrates an example flow diagram for determining tissue health through application of multiple varying amounts of forces in succession.

FIG. 6 illustrates an example flow diagram for determining tissue health through application of multiple varying amounts of forces in succession. In block 610, navigate a tool including a tip and a sensor positioned on the tip to a region of interest (ROI). In one example, the sensor is one of the following types of sensors: a pressure sensor, a force sensor, or an impedance sensor, etc.

In block 620, apply a plurality of successive forces through the tool to the myocardial tissue in the ROI, and holding each of the plurality of successive force for a duration of time. In one example, the duration of time is a cardiac cycle. In another example, the duration of time is greater than one cardiac cycle, for example, two or more cardiac cycles, or fractions thereof. In yet another example, the duration of time is less than one cardiac cycle. Thus, if three forces are applied, each application of a force is held on for the duration of time. Additionally, in one example, each successive force is greater than the previous successive force that was applied to the myocardial tissue in the ROI. One skilled in the art would understand that, in another example, the amplitude of each successive force decreases from the previously applied successive force and that this example is equally applicable to the present disclosure. In one example, the amplitude of each of the plurality of successive forces is measured by the sensor. In another example, the amplitude of each of the plurality of successive forces is estimated based on the deflection as measured by the sensor at the end of diastole.

In block 630, measure a plurality of deflections of the tip of the tool, wherein each of the plurality of deflections corresponds to each of the plurality of successive forces applied to the myocardial tissue in the ROI. In block 640, determine the health condition of the myocardial tissue based on the plurality of deflections. If deflection increases as the successive forces being applied also increases, then the myocardial tissue is healthy. If the deflections remain approximately constant even as the successive forces being applied increases, then the myocardial tissue is not healthy (e.g., scarred tissue, an infarct, etc.). In one example, the steps of blocks 610 through 640 are repeated for multiple regions of interest.

In one aspect, a tool including a tip and a sensor positioned on the tip is positioned in contact with the myocardial tissue. In one example, the tool is either an endocardial catheter or an epicardial catheter (e.g., for use in ablation) or a transvenous guide wire or stylet (e.g., for use for lead implantation). The sensor on the tip of the tool has the ability to simultaneously gather position and orientation (P & O) information. In one example, the sensor is an electromagnetic sensor. In another example, the sensor is an ultrasonic sensor. Although the present example uses a sensor for gathering position and orientation information, multiple sensors (e.g., one for gathering position information and one for gathering orientation information, etc.) may be used and still be within the scope and spirit of the present disclosure.

Figure 7:
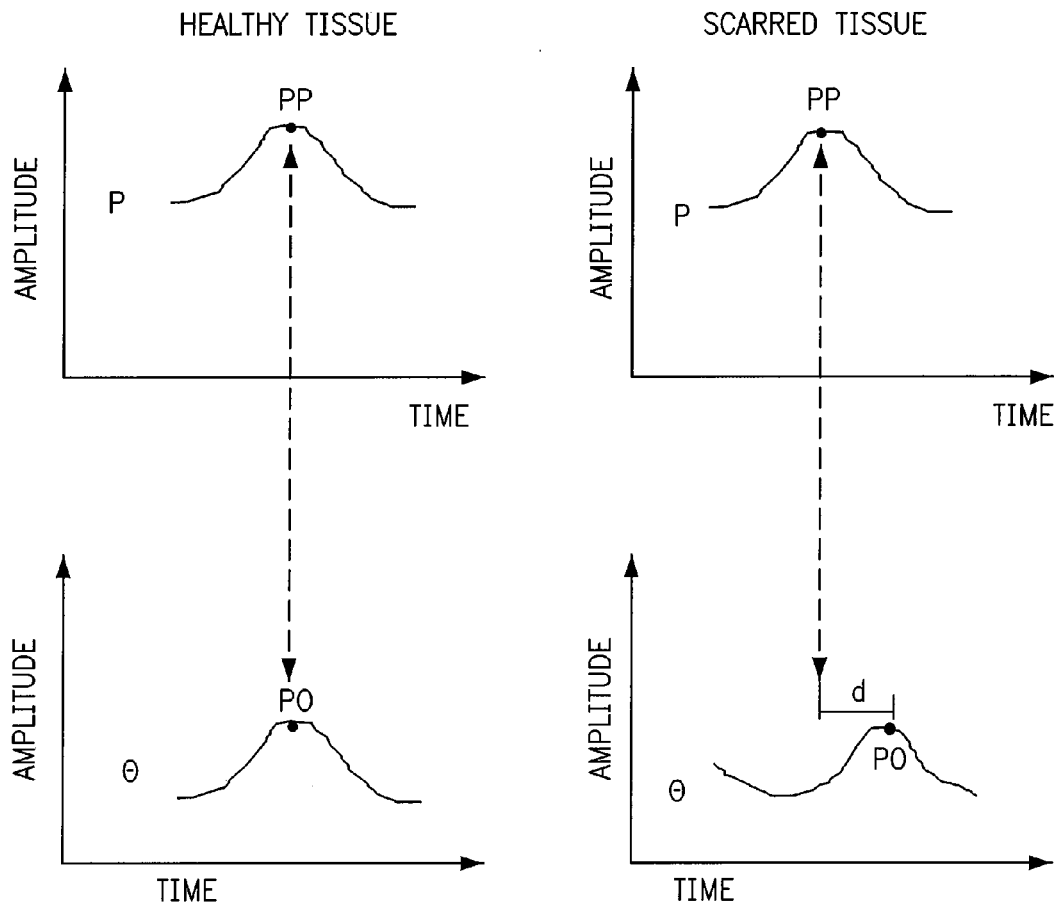
FIG. 7 illustrates an example graph showing peak position and peak orientation information of a healthy tissue contrasted with a scarred tissue (infarcted tissue).

For a given site of either ablation or lead implant interest, the sensor measures position and orientation (P & O) information for a plurality of heart beats. FIG. 7 illustrates an example graph showing peak position and peak orientation information of a healthy tissue contrasted with a scarred tissue (infarcted tissue). If there is a phase (temporal) difference between the peak position (maximum displacement) and the peak orientation (maximum angle) beyond a threshold, then the myocardial tissue of the site is labeled as infracted. In FIG. 7, peak position is denoted by "PP", and peak orientation is denoted by "PO". In FIG. 7, "d" represents the delay. An infarcted region (a.k.a. scarred region) of the myocardium with akinetic tissue would be subjected to a tethering effect, whereby the region of the myocardium would be passively "pulled along" by the neighboring contracting tissue. This "pulled along" characteristic causes a delay between the peak position and the peak orientation. The resulting delay is an indication of circumferential motion of active contraction by the neighboring healthy tissues.

In contrast, for a healthy region of myocardium, there is no phase (temporal) difference between the peak position and the peak orientation. See the graph on the left side of FIG. 7 where the peak position and peak orientation are aligned. For a healthy region, the peak position and peak orientation would be relatively aligned occurring within the threshold for infarct designation. In one example, an infarcted region would be a candidate for an ablation procedure, and a healthy region would be a candidate for lead implantation.

Figure 8:
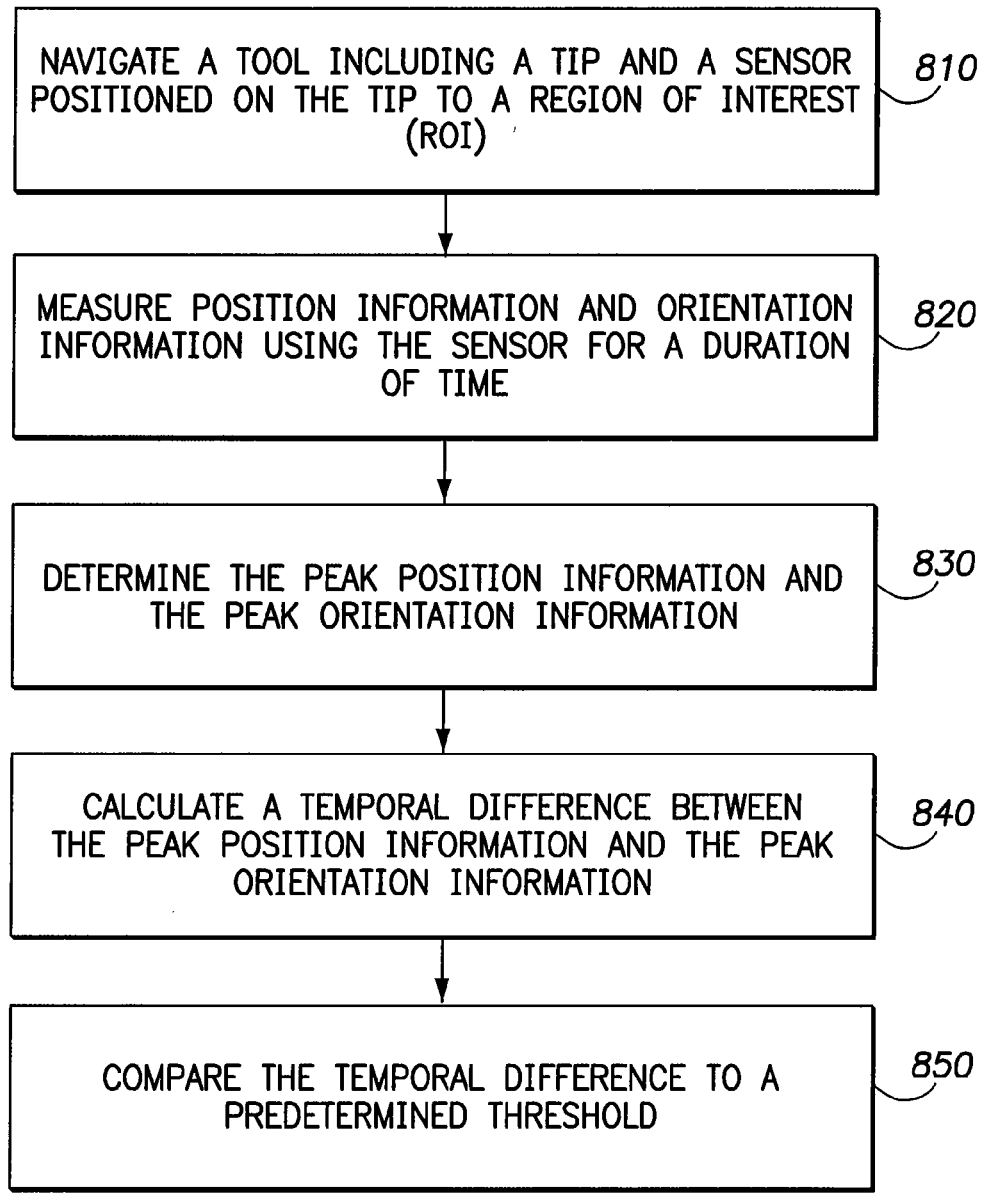
FIG. 8 illustrates an example flow diagram for measuring temporal difference of position and orientation information during a cardiac cycle.

FIG. 8 illustrates an example flow diagram for measuring temporal difference of position and orientation information during a cardiac cycle. In block 810, navigate a tool including a tip and a sensor positioned on the tip to a region of interest (ROI). In one example, the tool is an endocardial catheter or an epicardial catheter. In another example, the tool is a guide wire or a stylet. The sensor may be an electromagnetic sensor or an ultrasonic sensor. However, other tool types and/or sensor types may be used for the disclosed applications as understood by one skilled in the art.

In block 820, measure position information and orientation information using the sensor for a duration of time. In one example, the duration of time is a cardiac cycle. In block 830, determine the peak position information and the peak orientation information. In block 840, calculate a temporal difference between the peak position information and the peak orientation information. In one example, the temporal difference is expressed as an absolute time (i.e., milliseconds). In another example, the temporal difference is expressed as a relative time, for example, phase (i.e., fraction of a cardiac cycle, radians, etc.). In block 850, compare the temporal difference to a threshold. If the temporal difference is greater than the threshold, determine that the ROI as an infarct designation and may be a candidate for an ablation procedure. If the temporal difference is equal or less than the threshold, determine that the ROI as containing healthy tissue and may be is a candidate for lead implantation.

In one aspect, the tool used in the examples of the present disclosure may be the lead to be used for permanent implantation.

The steps illustrated in the flow diagrams of FIGS. 1, 5, 6 and 8 may be interchangeable and do not necessarily have to follow the flow illustrated. Also, some of the steps illustrated in the flow diagrams may be optional, such that deletion of some of the steps illustrated or additions of other steps not specifically illustrated herein will not affect the scope and spirit of the present disclosure as understood by one skilled in the art.

Since there is a degree of inference in labeling the akinetic substrate as an infarct scar or in labeling the substrate as healthy, in one example, to increase confidence about this labeling and improve assessment of tissue viability, a dobutamine or exercise stress test may be performed in conjunction with any of the presently disclosed procedures, in order to gain contractile reserve information for the region of interest (ROI). In one example, a coded substrate map (e.g., color-coded) of the ROI may be created in which each section of the tissue tested is coded on a pre-defined map to indicate its responsiveness and health. This map enables easy visualization of the healthy and akinetic areas for the medical personnel, and may be useful in guiding the medical personnel in their therapy localization to an optimal site of interest.

While for purposes of simplicity of explanation, the methodologies are shown and described as a series of acts, it is to be understood and appreciated that the methodologies are not limited by the order of acts, as some acts may, in accordance with one or more aspects, occur in different orders and/or concurrently with other acts from that shown and described herein. For example, those skilled in the art will understand and appreciate that a methodology could alternatively be represented as a series of interrelated states or events. Moreover, not all illustrated acts may be required to implement a methodology in accordance with one or more aspects.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

The invention claimed is:

1. A method for quantifying myocardial kinetics comprising:
   positioning a first sensor and a second sensor on respective myocardial substrate sites on opposing sides of a ventricular wall so that the first sensor is opposing the second sensor along the ventricular wall;
   tracking a relative displacement between the first sensor and the second sensor;
   computing a wall thickening of the ventricular wall based on the tracked relative displacement;
   determining whether the myocardial substrate site includes an infarct based on the wall thickening; and
   determining if the infarct is located closer to the myocardial substrate site on an endocardium or to the myocardial substrate site on an epicardium.

2. The method of claim 1, wherein the first sensor is epicardially-placed and the second sensor is endocardially placed, and the determining when the infarct is located closer to the endocardium or to the epicardium is based on whether the first sensor or the second sensor is more significantly displaced.

3. The method of claim 1, further comprising measuring a first absolute sensor displacement for the first sensor relative to a predefined reference midline and measuring a second absolute sensor displacement for the second sensor relative to the predefined reference midline.

4. The method of claim 3, wherein the determining if the infarct is located closer to the endocardium or to the epicardium is based on comparison of the first absolute sensor displacement and the second absolute sensor displacement.

5. The method of claim 1, further comprising determining transmurality of the infarct based on the relative displacement between the first sensor and the second sensor at at least two time points synchronized with one or more cardiac electrical signals.

6. The method of claim 5, wherein the one or more cardiac electrical signals is one or more of an electrocardiography (ECG) signals or intracardiac electrogram (IEGM) signals.

7. The method of claim 1, wherein the calculating operation includes calculating ventricular wall thickening represented as a percentage as $[(L_s-L_d)/L_s]*100$,
   where:
   $L_s$ is a distance between the first sensor and the second sensor as measured at end-systole; and
   $L_d$ is a distance between the first sensor and the second sensor as measured at end-diastole.

8. The method of claim 7, wherein the calculated ventricular wall thickening is used in determining whether the myocardial substrate site includes an infarct.

9. The method of claim 1, wherein the first sensor and second sensor are electromagnetic sensors, the tracking operation further comprising measuring electromagnetic field strengths for determining a distance between the first and second sensors as the relative displacements.

10. The method of claim 1, wherein one or both of the first sensor and the second sensor are positioned on the myocardial substrate site via a guide wire, a stylet or an electrophysiology catheter.

11. The method of claim 1, further comprising navigating at least one of the first and second sensors to multiple myocardiac substrate sites and repeating the steps of claim 1 a plurality of times in a region of interest (ROI) to create a map of the ROI for indicating the health condition of the myocardial substrate in the ROI.

* * * * *